United States Patent [19]

Rühl et al.

[11] Patent Number: 5,723,678
[45] Date of Patent: Mar. 3, 1998

[54] PREPARATION OF ACETYLENIC COMPOUNDS

[75] Inventors: Thomas Rühl, Frankenthal; Jochem Henkelmann, Mannheim; Marc Heider, Neustadt; Peter Hofmann, Nürnberg, all of Germany

[73] Assignee: BASF Aktiengesellschaft, Ludwigshafen, Germany

[21] Appl. No.: 631,095

[22] Filed: Apr. 12, 1996

[30] Foreign Application Priority Data

Apr. 12, 1995 [DE] Germany .................. 195 13 840.6

[51] Int. Cl.$^6$ .................................................. C07C 45/45
[52] U.S. Cl. ...................... 568/395; 568/349; 568/317; 568/8; 568/17
[58] Field of Search ..................... 568/8, 17, 395, 568/349, 317

[56] References Cited

U.S. PATENT DOCUMENTS

| | | | |
|---|---|---|---|
| 3,444,208 | 5/1969 | McClure | 568/317 |
| 4,173,590 | 11/1979 | Schmidbaur et al. | 568/8 |
| 4,753,912 | 6/1988 | Green | 568/8 |

OTHER PUBLICATIONS

Nikishin et al, Tetrahedron Letters, vol. 31, No. 48, pp. 7063–7064, 1990.
Tetrahedron Letters, vol. 31, No. 48, pp. 7065–7068, 1990, Highly Stereoselective Synthesis of . . . , Khripach et al.

*Primary Examiner*—James H. Reamer
*Attorney, Agent, or Firm*—Keil & Weinkauf

[57] ABSTRACT

Acetylenic compounds of the general formula I $$R^1\text{—}C\equiv C\text{—}CHR^2\text{—}CH_2\text{—}X \qquad I$$

where the substituents have the following meanings:
  $R^1$ hydrogen, unsubstituted or substituted alkyl or aryl;
  $R^2$ hydrogen or $C_1$–$C_4$-alkyl;
  X  CN; COOR$^3$ where $R^3$ is $C_1$–$C_6$-alkyl or benzyl;
     C(O)R$^4$ where $R^4$ is hydrogen or $C_1$–$C_4$-alkyl,
are prepared by reacting an alkyne of the formula II $$R^1\text{—}C\equiv C\text{—}H \qquad II$$

with an α,β-unsaturated compound of the formula III $$R^2HC\text{=}CH\text{—}X \qquad III$$

in the presence of a homogeneous rhodium-phosphine catalyst, in a process wherein a catalyst with a bidentate or tridentate phosphine compound is used.

4 Claims, No Drawings

PREPARATION OF ACETYLENIC COMPOUNDS

The present invention relates to an improved process for preparing acetylenic compounds of the general formula I $$R^1—C\equiv C—CHR^2—CH_2—X \quad\quad I$$

where the substituents have the following meanings:
$R^1$ hydrogen, unsubstituted or substituted alkyl or aryl;
$R^2$ hydrogen or $C_1$-$C_4$-alkyl;
X CN; $COOR^3$ where $R^3$ is $C_1$-$C_6$-alkyl or benzyl; $COR^4$ where $R^4$ is hydrogen or $C_1$-$C_4$-alkyl,
by reacting an alkyne of the formula II $$R^1—C\equiv C—H \quad\quad II$$

with an α,β-unsaturated compound of the formula III $$R^2HC=CH—X \quad\quad III$$

in the presence of a homogeneous rhodium-phosphine catalyst.

Kovalev et al. describe in Tetrahedron Letters 31 (1990) 7063 the reaction of alkynes such as hexyne and phenylacetylene with α,β-unsaturated ketones such as vinyl methyl ketone to give γ,δ-acetylenic ketones. The catalyst used is tris(trimethylphosphine) rhodium chloride. Satisfactory yields can be achieved only with long reaction times. The reaction times are in the region of several days and make transfer of the described process to the industrial scale prohibitive.

It is an object of the present invention to provide a process which makes it possible to prepare the products I in high yield and in shorter reaction times than in the prior art.

We have found that this object is achieved by the process, described at the outset, for preparing acetylenic compounds of the formula I, wherein a rhodium catalyst with a bidentate or tridentate phosphine compound is used.

The alkynes of the formula II to be used according to the invention are terminal alkynes. Suitable besides acetylene are alkyl-substituted, preferably $C_1$-$C_6$-alkyl-substituted, alkynes such as propyne, 1-butyne and 1-hexyne. It is furthermore possible to use an aryl-substituted, preferably phenyl-substituted, alkyne such as phenylacetylene. The alkyl and aryl radicals may have substituents which are inert under the reaction conditions, such as halogen and amino, but preferably hydroxyl. Examples of appropriate alkynes are 1-methylbutynol and propargyl alcohol. Particularly preferred alkynes are acetylene, hexane and propargyl alcohol.

The alkyne of the formula II is reacted with an α,β-unsaturated compound of the formula III. This can be, in the case where X is CN, a nitrile such as acrylontrile.

Also suitable are $C_1$-$C_6$-alkyl esters, preferably methyl and ethyl esters, and benzyl esters, of α,β-unsaturated acids, eg. methyl acrylate, ethyl acrylate, tert-butyl acrylate. Finally, α, β-unsaturated aldehydes and ketones such as methyl vinyl ketone, crotonaldehyde, cyclohexenone and 2(5H)-furanones may be mentioned.

Particularly preferred compounds of the formula III are methyl vinyl ketone, crotonaldehyde, ethyl acrylate and acrylonitrile.

As a rule, the starting compounds of the formulae II and III are reacted in equivalent ratios.

The reaction can take place in a solvent whose amount is, in general, from 5 to 90 % of the weight of the reaction mixture. Suitable for this purpose are ketones such as acetone, ethers such as tetrahydrofuran and methyl tert-butyl ether, aromatic hydrocarbons such as toluene, and aprotic polar solvents such as N-methylpyrrolidone.

The reaction is generally carried out at from 20° to 100° C., preferably 30° to 70° C., as a rule under atmospheric pressure, but the pressure can be up to 20 bar when acetylene is used.

The catalyst used is a homogeneous rhodium-phosphine complex. The phosphines are bidentate or tridentate, ie. the ligands to be used according to the invention have two or three tertiary trivalent phosphorus atoms which preferably carry non-aromatic radicals. The phosphorus atoms preferably carry $C_1$-$C_4$-alkyl radicals such as methyl, ethyl, n-propyl, isopropyl, n-butyl and tert.-butyl, and cyclohexyl. Bidentate phosphines whose phosphorus atoms are separated by a $C_1$-$C_3$-alkylene chain are preferably used, such as 1,2-bis(dicyclohexylphosphino) ethane, 1,2-bis (dicyclohexylphosphino)methane, 1,2-bis (dimethylphosphino)ethane, 1,2-bis(dimethylphosphino) methane, 1,2-bis(di-tert-butylphosphino)methane or 1,2-bis (diisopropylphosphino)propane.

Polydentate phosphines of these types are commercially available or can be prepared by methods disclosed in the literature.

The rhodium-phosphine complex is preferably prepared in situ. For this purpose, a bidentate or tridentate phosphine is reacted, preferably in equimolar amount or with an up to 20 mol % phosphine excess, with a suitable rhodium compound from which a rhodium-phosphine complex forms under the reaction conditions. Suitable rhodium compounds are cyclooctadienylrhodium chloride, rhodium acetylacetonate and rhodium chloride.

The amounts of rhodium are generally chosen to be from 0.01 to 0.1 mol % based on the alkyne of the formula II. The appropriate amounts can easily be established by the skilled worker in preliminary tests.

The starting compounds of the formula II and III, and the rhodium-phosphine complex or its precursors (ie. a phosphine and a rhodium compound which reacts to give the phosphine complex under the reaction conditions) and, where appropriate, a solvent can be mixed in a reactor, eg. a stirred vessel or, on use of acetylene, a pressure vessel, advantageously adding the alkyne as last component.

The reaction can be carried out either continuously or batchwise.

After a reaction time which is generally from 2 to 24 hours, the resulting mixture is worked up in a conventional way to the products of the formula I. The reaction mixture can be distilled to remove solvent and the product can then be separated from the catalyst. The latter can be returned, where appropriate after regeneration, to the reaction.

The process according to the invention permits acetylenic compounds of the formula I to be prepared in high yield with short reaction times.

The products of the formula I are used as precursors for additives in electroplating baths and as drug precursors.

EXAMPLES

General method of preparation 1.1 mmol of a phosphine ligand were added to 1 mmol of cyclooctadienylrhodium chloride in 30 ml of acetone and stirred for 30 minutes.

0.1–1 mol of the unsaturated compound of the formula III and 0.1–1 mol of the alkyne of the formula II were added to the solution.

After stirring at 50° C. for 12 h, the product was isolated by distillation.

The following table gives details of the reaction and the yields obtained.

| Unsaturated compound III (mol) | Alkyne compound II (mol) | Phosphine ligand | Yield (%) |
|---|---|---|---|
| MVK (0.1) | Hexyne (0.1) | dmpe | 96 |
| MVK (0.1) | Hexyne (0.1) | dmpm | 92 |
| MVK (0.1) | Hexyne (0.1) | dcype | 93 |
| MVK (0.1) | Hexyne (0.1) | dtbpm | 90 |
| MVK (0.1) | Acetylene (0.1) | dmpe | 55 |
| MVK (1) | Propargyl alcohol (1) | dmpe | 93 |
| MVK (1) | Methylbutynol (1) | dmpe | 92 |
| Crotonaldehyde (0.1) | Hexyne (0.1) | dmpe | 72 |
| Crotonaldehyde (0.1) | Acetylene (0.1) | dmpe | 34 |

MVK = Methyl vinyl ketone
dmpe = 1,2-bis(dimethylphosphino)ethane
dmpm = 1,2-bis(dimethylphosphino)methane
dcype = 1,2-bis(dicyclohexylphosphino)ethane
dtbpm = 1,2-bis(di-tert.-butylphosphino)methane

We claim:
1. A process for preparing acetylenic compounds of the general formula I

$$R^1-C{\equiv}C-CHR^2-CH_2-X \qquad I$$

where the substituents have the following meanings:
R$^1$ hydrogen, unsubstituted or substituted alkyl or aryl;
R$^2$ hydrogen or C$_1$–C$_4$-alkyl;
X CN; COOR$^3$ where R$^3$ is C$_1$–C$_6$-alkyl or benzyl; C(O)R$^4$ where R$^4$ is hydrogen or C$_1$–C$_4$-alkyl.
by reacting an alkyne of the formula II $$R^1-C{\equiv}C-H \qquad II$$

with an α,β-unsaturated compound of the formula III $$R^2HC{=}CH-X \qquad III$$

at a temperature from 20° C. to 100° C. in a solvent selected from the group consisting of ketones, ethers, aromatic hydrocarbons and aprotic solvents,
in the presence of a homogeneous rhodium-phosphine catalyst, wherein a rhodium catalyst with a bidentate phosphine ligand is used, the bidentate phosphine ligand being a member selected from the group consisting of 1,2-bis(dicyclohexylphosphino)ethane, 1,2-bis(dicyclohexylphosphino)methane, 1,2-bis(dimethylphosphino)ethane, 1,2-bis(dimethylphosphino)methane, 1,2-bis(di-tert-butylphosphino)methane or 1,2-bis(diisopropylphosphino)propane.

2. A process as claimed in claim 1, wherein vinyl methyl ketone, crotonaldehyde or a C$_1$–C$_6$-alkyl acrylate is used as α,β-unsaturated compound of the formula III.

3. A process as claimed in claim 1, wherein acetylene, propargyl alcohol or hexyne is used as alkyne of the formula II.

4. A process as claimed in claim 2, wherein acetylene, propargyl alcohol or hexyne is used as alkyne of the formula II.

* * * * *